US010904973B2

(12) United States Patent
Sattler (10) Patent No.: US 10,904,973 B2
(45) Date of Patent: Jan. 26, 2021

(54) LIGHTING DEVICE, OPERATING LIGHT, PROCESS AND COMPUTER PROGRAM FOR CONTROLLING A PLURALITY OF LIGHTING ELEMENTS IN A LIGHTING DEVICE

(71) Applicant: Drägerwerk AG & Co. KGaA, Lübeck (DE)

(72) Inventor: Frank Sattler, Lübeck (DE)

(73) Assignee: Drägerwerk AG & Co. KGaA, Lübeck (DE)

(*) Notice: Subject to any disclaimer, the term of this patent is extended or adjusted under 35 U.S.C. 154(b) by 0 days.

(21) Appl. No.: 16/216,041

(22) Filed: Dec. 11, 2018

(65) Prior Publication Data

US 2019/0191511 A1 Jun. 20, 2019

(30) Foreign Application Priority Data

Dec. 15, 2017 (DE) .................. 10 2017 011 624

(51) Int. Cl.
| | | |
|---|---|---|
| H05B 45/325 | (2020.01) | |
| H05B 45/10 | (2020.01) | |
| H05B 47/165 | (2020.01) | |
| H05B 45/37 | (2020.01) | |
| H05B 47/19 | (2020.01) | |

(52) U.S. Cl.
CPC ............. H05B 45/37 (2020.01); H05B 45/10 (2020.01); H05B 47/19 (2020.01)

(58) Field of Classification Search
None
See application file for complete search history.

(56) References Cited

U.S. PATENT DOCUMENTS

| | | | |
|---|---|---|---|
| 9,504,113 B2 | 11/2016 | Sattler et al. | |
| 2003/0185009 A1* | 10/2003 | Walters | A61B 90/30 362/276 |
| 2004/0129860 A1* | 7/2004 | Thibaud | A61B 90/30 250/205 |
| 2009/0261759 A1* | 10/2009 | Fornasiero | A61B 90/30 315/307 |

(Continued)

FOREIGN PATENT DOCUMENTS

| | | |
|---|---|---|
| CN | 101233362 A | 7/2008 |
| CN | 104582623 A | 4/2015 |

(Continued)

*Primary Examiner* — Henry Luong
(74) *Attorney, Agent, or Firm* — McGlew and Tuttle, P.C.

(57) ABSTRACT

A lighting device (10) is provided along with an operating light and a process (50), including a process with a computer program, controlling a plurality of lighting elements in a lighting device (10). The lighting elements are divided into a plurality of groups of lighting elements (20*a*; 20*b*; 20*c*; 20*d*; 20*e*; 20*f*; 20*g*), with each group of lighting elements (20*a*; 20*b*; 20*c*; 20*d*; 20*e*; 20*f*; 20*g*) including at least two lighting elements. The process (50) includes assigning (52) different characteristics (30*a-h*) to the groups of lighting elements (20*a*; 20*b*; 20*c*; 20*d*; 20*e*; 20*f*; 20*g*). A characteristic (30*a-h*) includes a sequence of different light intensities in temporal subintervals. The process (50) further includes an activation (54) of subsets of lighting elements in the groups of lighting elements (20*a*; 20*b*; 20*c*; 20*d*; 20*e*; 20*f*; 20*g*) in the temporal subintervals based on light intensities.

22 Claims, 6 Drawing Sheets

(56) References Cited

U.S. PATENT DOCUMENTS

| | | | | |
|---|---|---|---|---|
| 2011/0309754 A1* | 12/2011 | Ashdown | ............... | H05B 45/37 |
| | | | | 315/151 |
| 2013/0257287 A1* | 10/2013 | Pi | ....................... | H05B 33/0818 |
| | | | | 315/151 |
| 2016/0327227 A1* | 11/2016 | Green, Jr. | ............. | F21S 10/043 |
| 2017/0372530 A1* | 12/2017 | Clemente | ........... | G07C 9/00309 |

FOREIGN PATENT DOCUMENTS

| | | |
|---|---|---|
| DE | 10 2012 206 889 A1 | 10/2013 |
| DE | 10 2012 014 907 A1 | 1/2014 |
| DE | 10 2012 014 716 A1 | 5/2014 |

* cited by examiner

LIGHTING DEVICE, OPERATING LIGHT, PROCESS AND COMPUTER PROGRAM FOR CONTROLLING A PLURALITY OF LIGHTING ELEMENTS IN A LIGHTING DEVICE

CROSS REFERENCE TO RELATED APPLICATIONS

This application claims the benefit of priority under 35 U.S.C. § 119 of German Application 10 2017 011 624.5, filed Dec. 15, 2017, the entire contents of which are incorporated herein by reference.

TECHNICAL FIELD

Exemplary embodiments pertain to a lighting device, an operating light, a process and a computer program for controlling a plurality of lighting elements in a lighting device, and especially but not exclusively, to a concept for the spatially modulated actuation of lighting elements of a lighting device.

BACKGROUND

There are many applications for lighting devices in the medical field, for example, in outpatient and inpatient examination facilities. Adequate lighting is of great importance particularly in intensive care units and in operating rooms. For example, operating lights are used in an operating room to light the operating area (e.g., the surgical wound) as uniformly as possible and as constantly as possible over time.

However, this illumination may be impaired by objects in the beam path, e.g., a shadow may form when the head of the surgeon is located between the operating light and the surgical wound. In order to reduce these shadowing effects, an operating light or lighting device in the medical field usually consists of, among other things, a large number of individual illuminants (usually combined into modules), which shall illuminate the surgical wound from different directions. For example, such a lighting device consists of 108 LEDs (light-emitting diodes), which are installed in 54 precession reflectors.

To reduce the shadows, the light may be equipped with a number of detectors, which are typically located in the spatial vicinity of the individual illuminants. The object of the detectors in this case is to detect the back-scattered light components in order to detect therefrom objects in the beam path of the light by means of suitable mathematical processes. The illumination can then be improved and the shadowing can be reduced by means of suitable readjustment of the illumination intensities of the individual illuminants.

Further details regarding this can be found, for example, in the publication DE 10 2012 014 716 A1.

SUMMARY OF THE INVENTION

There is a need to provide an improved concept for a lighting device. Exemplary embodiments of a lighting device, an operating light and a process according to the invention meet this need.

Exemplary embodiments are based on the discovery that existing concepts in the control of intensity of lighting devices use a temporal modulation of the lighting elements with a modulation frequency and a scanning frequency for the detection of reflected light, which can be reduced with a spatial modulation. A basic idea of exemplary embodiments of a group of lighting elements is to actuate only a subset of the lighting elements to obtain a predefined light intensity. A modulation frequency and/or scanning frequency can be reduced by this selection of a subset instead of an actuation of all lighting elements simultaneously with an interruption corresponding to the light intensity.

Exemplary embodiments provide a process for controlling a plurality of lighting elements in a lighting device. The lighting elements are divided into a plurality of groups of lighting elements and a group of lighting elements comprises at least two lighting elements. The process comprises an assignment of different characteristics to the groups of lighting elements, wherein a characteristic has a characteristic duration and comprises a sequence of different light intensities in temporal subintervals. The process further comprises an activation of subsets of lighting elements in the groups of lighting elements in the temporal subintervals based on the light intensities. Due to the activation of a subset, a light intensity can be formed by a ratio of simultaneously activated and deactivated lighting elements. An activation and deactivation over time of all lighting elements for controlling the intensity can thus be reduced or even completely eliminated, as a result of which, for example, a scanning rate in the detection of reflected light can be reduced.

Activation of a subset of lighting elements of a group of lighting elements may comprise an activation of at least one lighting element of the group of lighting elements and a simultaneous deactivation of at least one other lighting element of the group of lighting elements in a subinterval, when a light intensity in the temporal subinterval is a minimal light intensity. A reduced light intensity can be generated due to the simultaneous activation and deactivation of the lighting elements without the lighting durations of the lighting elements being modulated over time. The different light intensities may comprise at least one high light intensity and one low light intensity. In a subinterval with low light intensity, at least one lighting element of a group of lighting elements may then be activated and another lighting element of the group of lighting elements may be deactivated simultaneously. Another modulation over time within the subinterval for generating a defined light intensity may then be omitted or, in addition, may take place to an adapted extent.

In exemplary embodiments, the activation of the subset may correspond to a spatial modulation of the lighting elements of a group of lighting elements based on the light intensities. In this respect, spatially distributed lighting elements can be activated and other lighting elements can be deactivated within the groups of lighting elements. The groups of lighting elements may be arranged in a spatially or geometrically separated manner, wherein the groups of lighting elements may be separated logically based on the characteristics. For example, the characteristics may correspond to Walsh functions.

In some exemplary embodiments, the process may further comprise a variation of the activated lighting elements of the subset of a group of lighting elements, which may bring about an equalization of lighting durations of the lighting elements. Such an equalization may take place within a subinterval or even in a different temporal interval. A characteristic has, for example, a characteristic duration and the equalization of the lighting durations may take place over one or more characteristic durations. E.g., the equalization of the lighting durations may also take place over a period of time that is longer than a characteristic duration. Thus, longer temporal intervals for the equalization of the lighting durations of the lighting elements may also be provided in exemplary embodiments. The equalization of the lighting durations of the lighting elements may extend the service life of a lighting device or bring about a more uniform generation of heat.

In other exemplary embodiments, the process may further comprise a detection of objects in a beam path of the lighting device and a control or regulation of the groups of lighting elements based on the objects. Thus, exemplary embodiments can make possible a modulation of shadows. In some exemplary embodiments, the activation of the subset of a spatial modulation of the lighting elements of a group of lighting elements may correspondingly correspond to the light intensities and a temporal modulation of the lighting elements of a group of lighting elements may additionally take place. Some exemplary embodiments may consequently make possible a finer granularity of light intensities during the actuation of groups of lighting elements. The spatial modulation and the temporal modulation may take place simultaneously and/or at different times in the exemplary embodiments.

Another exemplary embodiment is a computer program with a program code for executing one of the processes being described here, when the program code is executed on a computer, a processor or a programmable hardware component.

Exemplary embodiments also provide a lighting device with a plurality of lighting elements. The lighting elements are divided into a plurality of groups of lighting elements and a group of lighting elements comprises at least two lighting elements. The lighting device further comprises a controller for carrying out one of the processes being described here. The lighting elements may be, for example, printed LEDs, which can be arranged in almost any desired geometric patterns in a cost-effective manner. Exemplary embodiments provide, moreover, an operating light with such a lighting device.

Other advantageous embodiments are described in more detail below on the basis of the exemplary embodiments shown in the drawings, to which all of the exemplary embodiments are generally not limited, however.

In the following description of the attached figures, which show only some examples of exemplary embodiments, identical reference numbers may designate identical or comparable components. Further, summary reference numbers may be used for components and objects that are present as a plurality of components or objects in an exemplary embodiment or in a drawing, but are described together with respect to one or more features. Components or objects which are described with the same or summary reference numbers may have identical configuration but possibly also different configurations in respect to individual features, a plurality of features or all features, for example, their dimensions, unless something different appears explicitly or implicitly from the description. Optional components are shown by broken lines or arrows in the figures.

The same reference numbers designate identical or similar components in the entire description of the figures. Even though exemplary embodiments may be modified and varied in different manners, exemplary embodiments are shown as examples in the figures and will be described in detail. However, it should be made clear that exemplary embodiments are not intended to be limited to the respective disclosed forms, but exemplary embodiments shall rather cover all functional and/or structural modifications, equivalents or alternatives, which are within the scope of the present invention. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
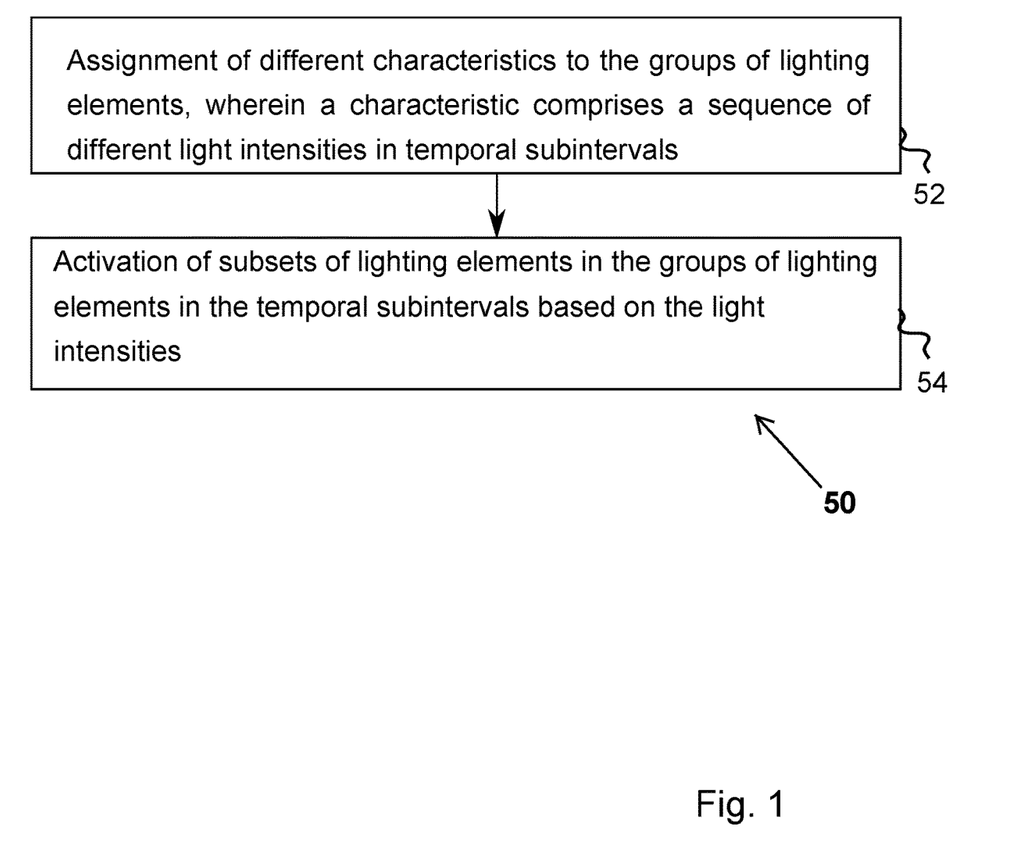
FIG. 1 is a block diagram of an exemplary embodiment of a process for controlling a plurality of lighting elements in a lighting device.

Referring to the drawings, FIG. 1 illustrates a block diagram of an exemplary embodiment of a process for controlling a plurality of lighting elements in a lighting device. The process 50 is configured for controlling a plurality of lighting elements in a lighting device 10. The lighting elements are divided into a plurality of groups of lighting elements 20a-g and each group of lighting elements 20a-g comprises at least two lighting elements. The process comprises an assignment 52 of different characteristics 30a-h to the groups of lighting elements 20a-g, wherein a characteristic 30a-h comprises a sequence of different light intensities in temporal subintervals. The process further comprises an activation 54 of subsets of lighting elements in the groups of lighting elements 20a-g in the temporal subintervals based on the light intensities.

Figure 2:
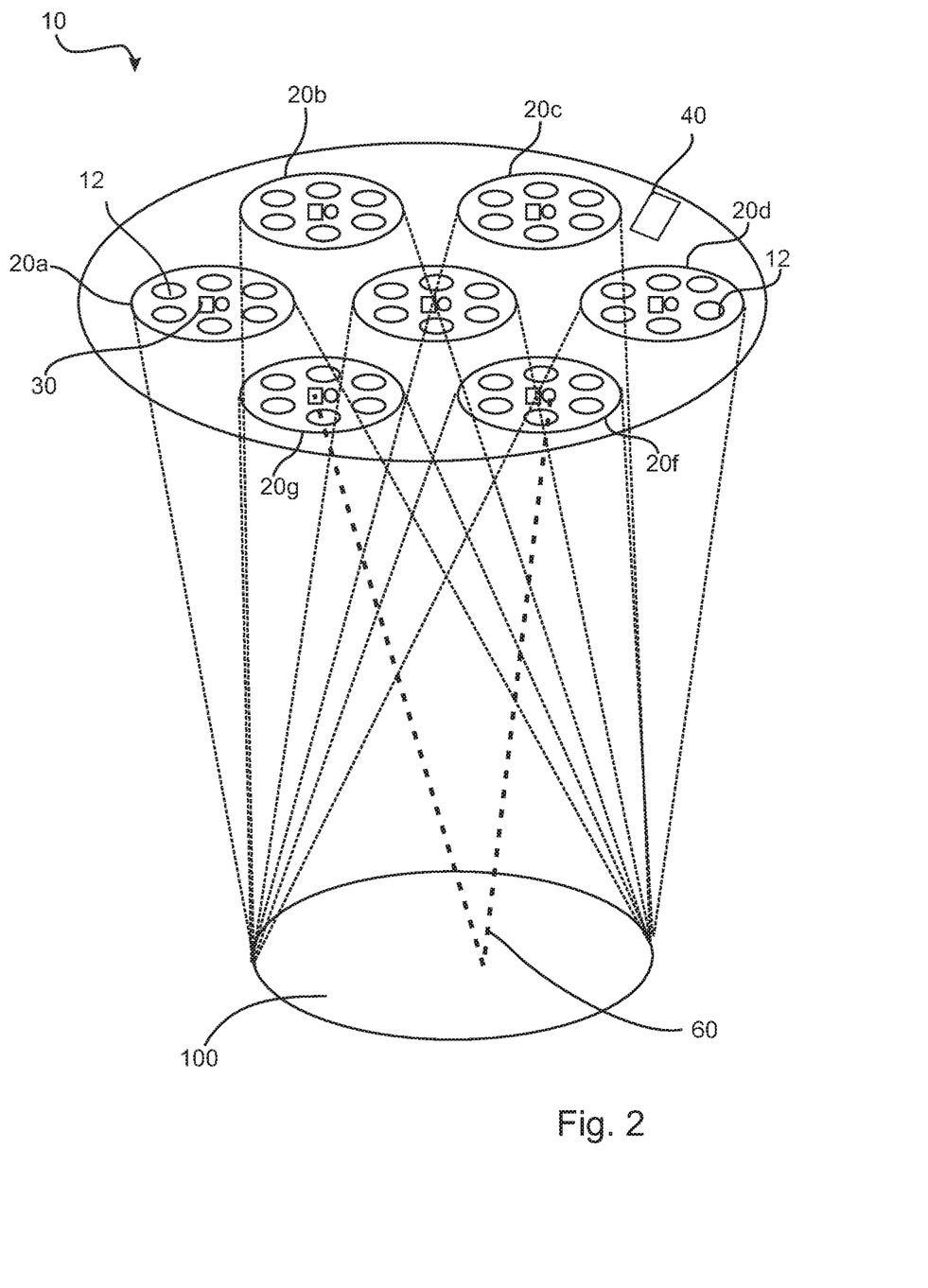
FIG. 2 is a schematic view showing an exemplary embodiment of a lighting device.

FIG. 2 shows an exemplary embodiment of a lighting device 10 with a plurality of lighting elements (illuminants) 12, wherein the lighting elements 12 are divided into a plurality of groups of lighting elements 20a-g and wherein a group of lighting elements 20a-g comprises at least two lighting elements 12. The lighting device 10 further comprises a controller 40 for carrying out one of the processes 50 being described here. The controller 40 comprises a computer, namely one or more processors with associated memory and with signal connections to the light elements 12. The controller 40 is also signal connected to one or more detectors 30 as described in U.S. Pat. No. 9,504,113. The lighting elements 12 may be implemented, for example, as light-emitting diodes (LEDs), wherein other lighting elements 12 or light sources may be used instead. Printed LEDs, which can be manufactured and processed in a cost-effective manner, may comprise the lighting elements 12 in some exemplary embodiments. As FIG. 2 further shows, the individual groups of lighting elements 20a-g may be arranged in a spatially or geometrically separated manner. In this connection, FIG. 2 shows an island-like arrangement of the lighting elements 12 in the groups of lighting elements 20*a-g*, wherein the dotted lines indicate the individual illumination cones of the groups of lighting elements 20*a-g*. The lighting device 10 is comprised in an operating light in the exemplary embodiment.

FIG. 2 shows a total of seven groups 20*a-g* of lighting elements 12. Each of the groups is designated with one of the individual reference numbers 20*a*, 20*b*, 20*c*, 20*d*, 20*e*, 20*f* and 20*g*. Each group of lighting elements 20*a-g* may have a modular configuration and the individual modules may then be combined to form the lighting device 10. In one exemplary embodiment, such a light module may be provided with a plurality of lighting elements 12, which may especially be LEDs. In addition, each module or each group of lighting elements 20*a-g* may have an associated detector 30 for the detection of reflected light. In addition, the computer 40 may be provided, which may execute a process being described here. Another exemplary embodiment of the process provides a computer program with a program code for executing one or more of the process steps of the processes 50 being described here when the program code is executed on a computer, on a processor or on a programmable hardware component.

The computer, regulator or controller 40 may in this respect be implemented as a computer, processor or programmable hardware component. The lighting device may comprise any desired controller or processor or a programmable hardware component in the exemplary embodiments. The process 50 may be embodied as software, which is programmed for a corresponding hardware component. The computer or controller 40 may in this respect be implemented as programmable hardware with correspondingly adapted software. In this connection, any desired processors, such as digital signal processors (DSPs) may be used. Exemplary embodiments are not limited here to a defined type of processor. Any desired processors or a plurality of processors may be used for implementation. In this connection, it is further conceivable for some exemplary embodiments that the computing power is not made available locally at the device (lighting device or operating light), but rather is implemented in a spatially separated manner. For example, the controller, regulator or computer 40 may also be disposed away from the groups of groups of lighting elements 20*a-g*. The groups of lighting elements 20*a-g* are connected to the computer 40 via a transmitter and receiver disposed adjacent to the groups of lighting elements 20*a-g* (e.g., via an Internet connection interface or via any of various communication interfaces). In some exemplary embodiments, implementations with cloud computing (cloud in the sense of distributed or spatially separated computing capacities) may be provided.

In the present exemplary embodiment, a characteristic illuminant, which is characterized by the characteristic 30*a-h* already mentioned above, is generated starting from each light module or each group of lighting elements 20*a-g*. This characteristic illuminant or a characteristic is especially characteristic with respect to the pulse width modulations used. FIG. 2 schematically shows a situation, in which all light modules cast their light on a common illumination area 100. This illumination area 100 is, e.g., the operating area of a surgeon during a surgical procedure. A first beam path is shown as a detection beam path 60 in FIG. 2, which, starting from the group of lighting elements 20*f*, reaches the illumination area 100, is reflected there and is again detected by all detectors. This detection beam path 60 can be defined in many ways and is shown in FIG. 2 only as an example. Thus, a detection beam path 60 will run from each lighting element to all other detectors as well as to its own detector. The plurality of possible beam paths makes it possible not to illustrate them because the clarity of the figure would otherwise be lost. Further details on lighting devices 10 of this type may also be found in DE 10 2012 014 716 A1 corresponding to U.S. Pat. No. 9,504,113 (B2). The entire contents of U.S. Pat. No. 9,504,113 (B2) are incorporated herein by reference.

LEDs advantageously are used as light elements (illuminants) 12. The brightness (light intensity) of such LEDs 12 may be set by means of a pulse width modulation (PWM). In case of a PWM, the average brightness of the LED is fixed via the duty cycle (ratio of pulse duration to period length) by the LED being switched on for a defined time (pulse duration) and being switched off for a defined time (period duration-pulse duration). A PWM is used with LEDs, for example, to make the light color not dependent on the set brightness and in order to be able to easily vary the brightness in a broad range.

Figure 3:
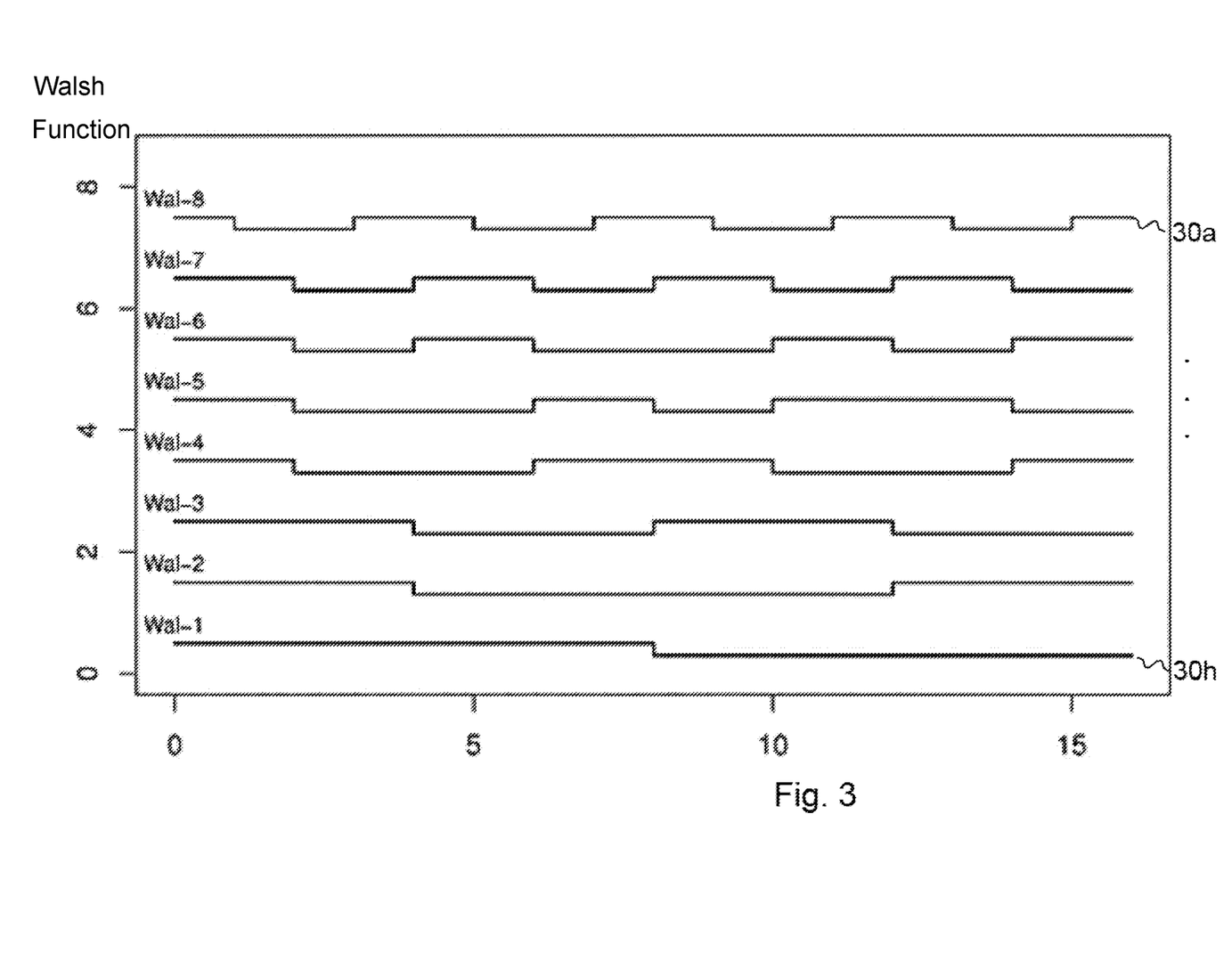
FIG. 3 is a view showing a group of eight characteristics in an exemplary embodiment.

In order to achieve the shadow compensation mentioned above, for example, individual illuminants (typically a group of lighting elements of LEDs, e.g., four pieces) are provided with brightness signatures (brightness modulation) or characteristics 30*a-h*, so that the individual illuminants can later be filtered out or separated from the received signals of the detectors. Many characteristic functions are conceivable for this. E.g., Walsh functions are suitable. FIG. 3 shows the case of eight such Walsh functions. FIG. 3 shows a group of eight characteristics 30*a-h* in an exemplary embodiment. FIG. 3 shows a curve of the characteristics 30*a-h* over time in 16 subintervals. The characteristics 30*a-h* are Walsh functions in this exemplary embodiment, but may also be any other desired orthogonal or even non-orthogonal function in other exemplary embodiments. The characteristics may be used to be able to identify the individual light signals in regard to the group of lighting elements 20*a-g* from which they originate, especially in the signals generated by detectors 30. In other words, an intensity of the reflected light is measured as a measured variable in case of control or regulation via the detectors 30. The contributions of the individual groups of lighting elements 20*a-g* to the overall reflected intensity may then be determined via the respective characteristics.

Figure 4:
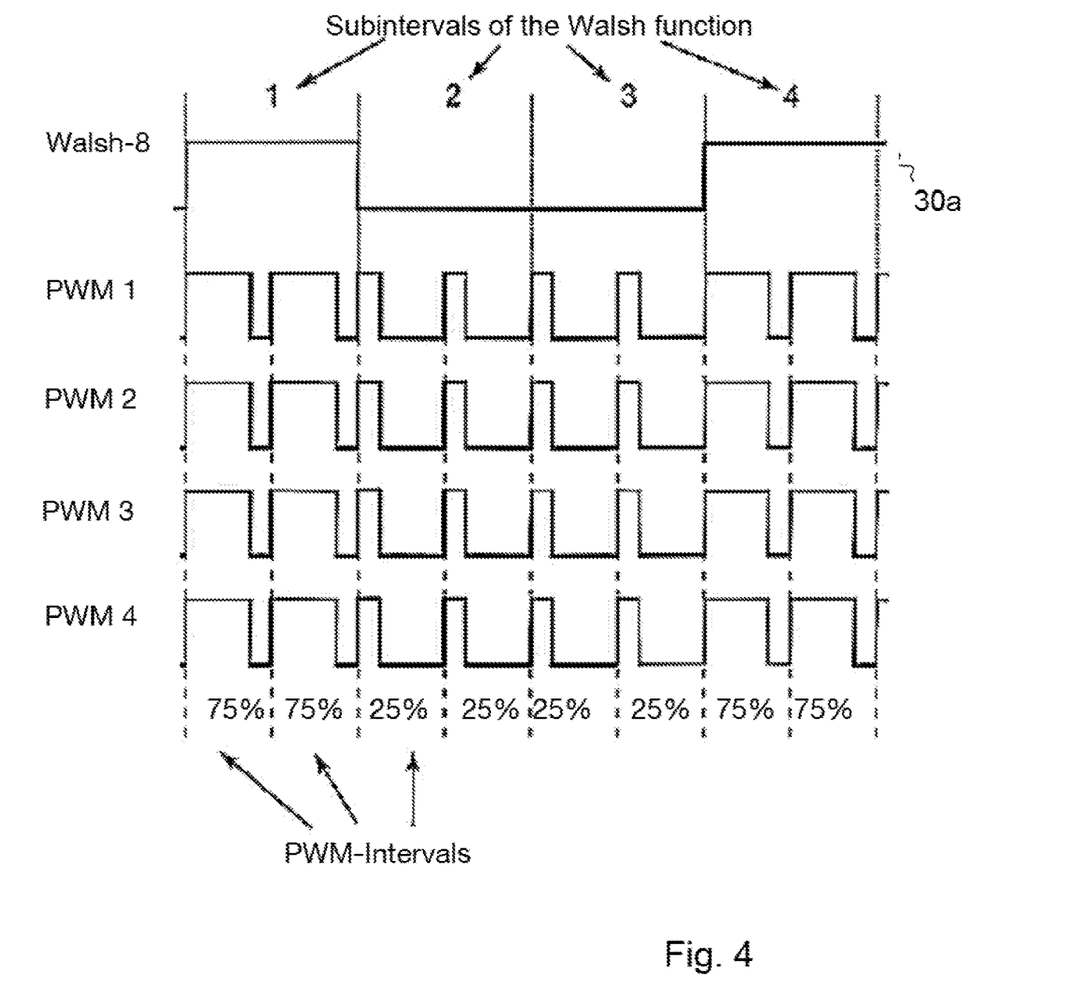
FIG. 4 is a view showing temporally modulated actuating signals.

FIG. 3 shows a period (consisting of 16 subintervals) of the Walsh functions. The function curves overall here are divided into 16 subintervals, in which each function/characteristic 30*a-h* has a constant value. In the example of the Walsh function No. 8, 30*a*, at the very top in FIG. 3, it is shown how PWM signals can be defined therefrom for the first four subintervals in FIG. 4. FIG. 4 shows temporally modulated actuating signals. FIG. 4 illustrates four light sources (LEDs) 12, for example, in the group of lighting elements 20*a*, to which the characteristic 30*a* is assigned, and wherein, for example, two PWM intervals are shown per Walsh subinterval. If the Walsh function has the value +1, then the duty cycle in this example is 75%, and the duty cycle is 25% in case of a function value −1 (the corresponding values are indicated in the PWM intervals). The brightness or light intensity of the LEDs 12 is then correspondingly changed. The curves shown are regarded here as time signals.

Exemplary embodiments therefore provide a process for the intensity modulation of light sources by means of pulse width modulation, wherein this pulse width modulation may be carried out not only temporally but also spatially. For this, the light source to be modulated typically consists of LEDs, i.e., of a plurality of light sources (illuminants) 12. A different duty cycle of the PWM is achieved in this case by only some of the light sources 12 being switched on. This can be utilized in order to achieve a shadow compensation in case of operating lights. In exemplary embodiments, a brightness control and/or brightness modulation can be especially carried out in the field of operating lights. In this case, the optical signals may be in the visible range and in the invisible range, and especially in the infrared range.

As can be seen in FIG. 4, the length of the Walsh subinterval is selected as a whole multiple (two in the example) of the period duration of the PWM in case of such a purely temporal modulation. In addition, the PWM frequency should be high enough (typically >80 Hz) in case of applications in the visible wavelength range, so that a person does not perceive flickering. In order to detect the correct brightness value/light intensity (percentage), these time signals should be scanned over time at the recipient (detectors 30) in a sufficiently fine manner. The number of steps of the duty cycles determines the minimal number of scanned values that are needed. This generally leads to relatively high scanning frequencies.

Numerical examples for the configuration shown in FIG. 4 are:
   duration of a Walsh function: 16 msec,
   duration of a Walsh subinterval: 1 msec,
   duration of a PWM interval: 0.5 msec,
   number of steps of the duty cycles: 5,
   duration of a step: 0.125 msec, and
   minimum necessary scanning frequency: 8,000 Hz.

Figure 5:
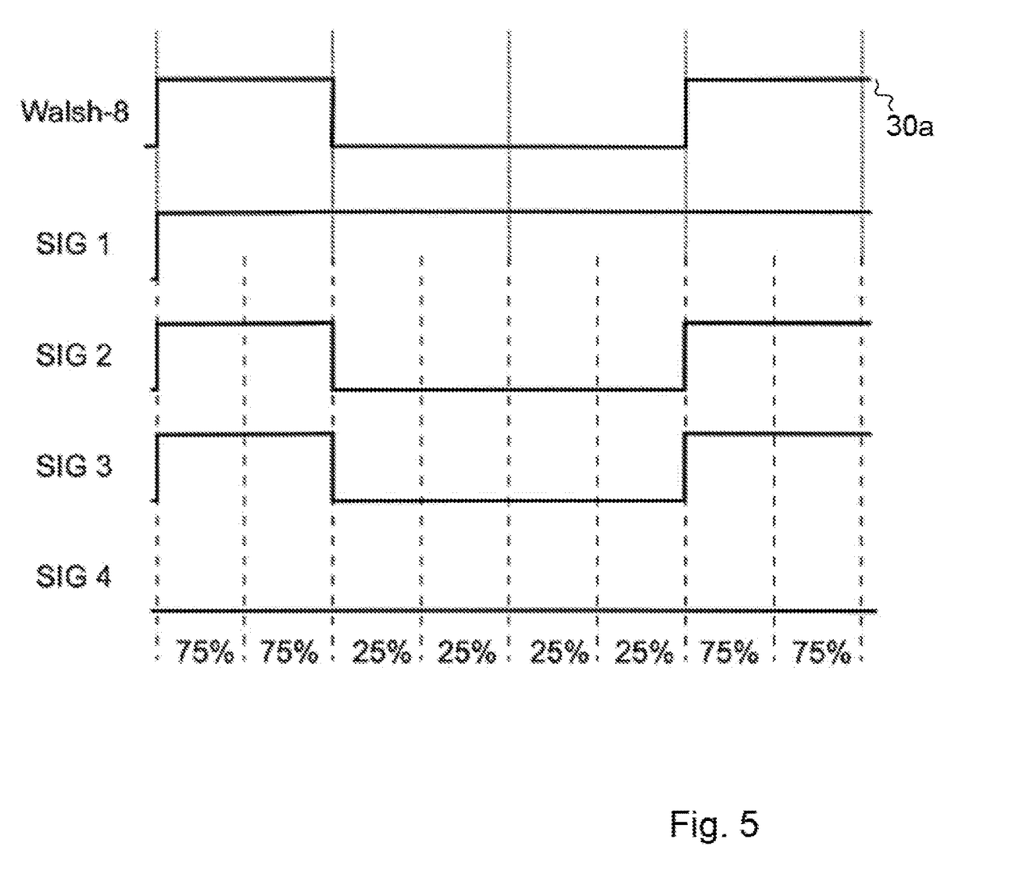
FIG. 5 is a view showing spatially modulated actuating signals in an exemplary embodiment.

Exemplary embodiments make possible a brightness control, which provides a spatial modulation in addition to or instead of the temporal PWM explained above. This spatial modulation may be used in addition to or as an alternative to the temporal modulation in the exemplary embodiments. As a result, the necessary scanning frequency can be reduced in at least some exemplary embodiments. Instead of all partial illuminants 12 of a group 20a-g, to which a certain Walsh function is assigned to, applying the same time signal, the partial illuminants or lighting elements 12 of a group of lighting elements receive different signals in the exemplary embodiments. Again using the example of four partial illuminants (LEDs), FIG. 5 shows a first variant, wherein again the Walsh function No. 8 is used as the basis. FIG. 5 shows spatially modulated actuating signals in an exemplary embodiment. The curve 30a of the Walsh function No. 8 is shown at the top in FIG. 5 and the curves over time of the four actuating signals SIG 1, SIG 2, SIG 3 and SIG 4 for four lighting elements of the group 20a are shown at the bottom. In order to reach 75% brightness, three of the four partial illuminants are switched on and one is switched off for the entire duration of the PWM interval.

In this exemplary embodiment, the activation of a subset of lighting elements of a group of lighting elements 20a-g comprises an activation of at least one lighting element of the group of lighting elements 20a-g (here SIG 1) and a simultaneous deactivation of at least one other lighting element of the group of lighting elements 20a-g in a subinterval (here SIG 2-4), if a light intensity in the temporal subinterval is a minimal light intensity (here 25%). In the exemplary embodiments, the different light intensities may generally comprise at least one high light intensity and one low light intensity (here 75% and 25%), wherein at least one lighting element of a group of lighting elements 20a-g is activated (here SIG 1) and another lighting element of the group of lighting elements 20a-g is deactivated (here SIG 2-4) simultaneously in a subinterval with low light intensity. The activation of the subset corresponds, in this case, to a spatial modulation of the lighting elements of a group of lighting elements 20a-g corresponding to the light intensities (here 75%, 25%). The granularity of the light intensities may generally be finer than 25% increments, for example, 1%, 2%, 5%, 10%, etc. In the same way, the number of lighting elements per group of lighting elements (illuminants) 12 may be a different number, e.g., 3, 5, 6, 10, 20, 50, 100, 500, etc. In addition, the number of lighting elements (illuminants) 12 in the different groups of lighting elements 20a-g may be different. As already explained on the basis of FIG. 2, the groups of lighting elements 20a-g may be arranged in a spatially or geometrically separated manner. The groups of lighting elements 20a-g are logically separated (distinguishable) based on the characteristics 30a-h in the present exemplary embodiment.

Figure 6:
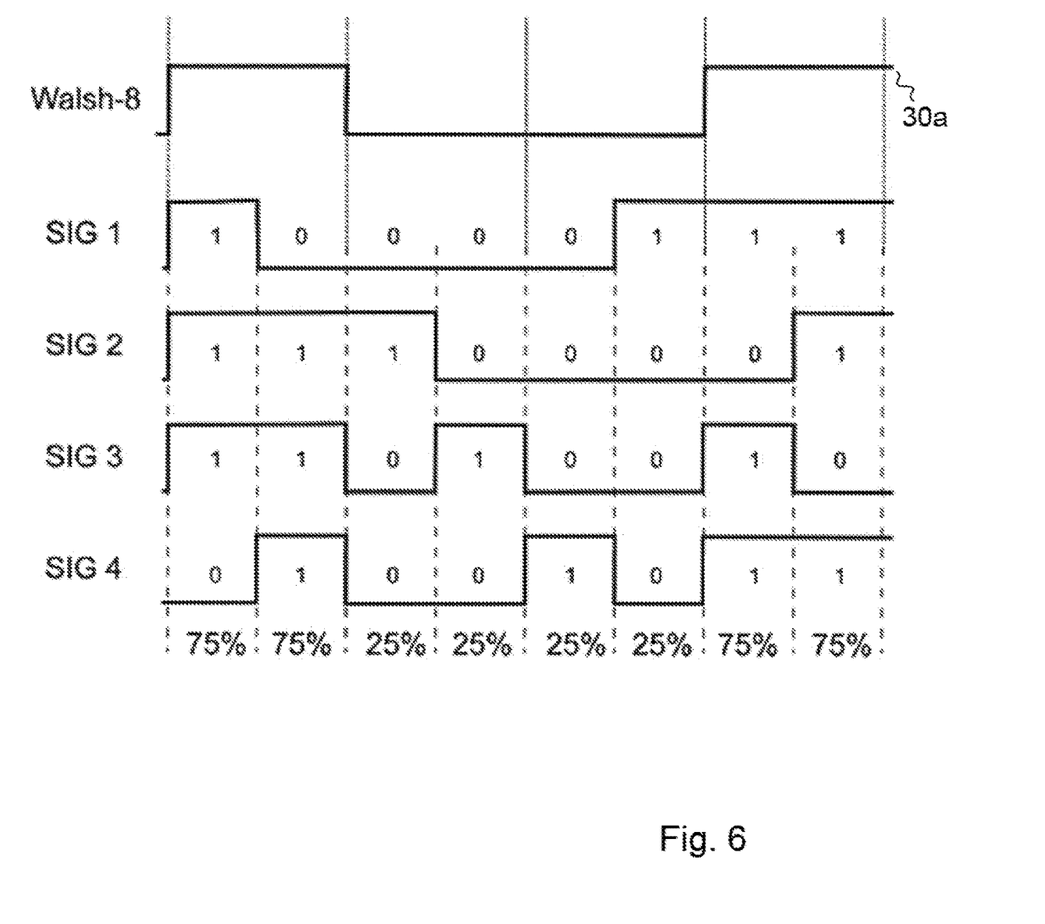
FIG. 6 is a view showing spatially modulated actuating signals in another exemplary embodiment.

As FIG. 5 further shows, the time signals of the partial illuminants/lighting elements (SIG 1 through SIG 4) are different. At 25% brightness, only one partial illuminant is switched on and three partial illuminants are switched off. In order to avoid one or more partial illuminants always being switched on and others always being switched off, the assignment may also vary over time. Such an exemplary embodiment is shown in FIG. 6. FIG. 6 shows spatially modulated actuating signals in another exemplary embodiment. The process in this exemplary embodiment comprises a variation of the activated lighting elements of the subset of a group of lighting elements 20a-g. The variation may comprise an equalization of lighting durations of the lighting elements. A uniform utilization of the lighting elements may increase the overall service life and life expectancy of the lighting device, as well as equalize the generation of heat. For this, an equalization of the lighting durations of the lighting elements over a plurality of time scales is conceivable. For example, the equalization may take place within a subinterval. For example, a characteristic 30a-h may have a characteristic duration; the 16 msec mentioned above are an example of this. The equalization of the lighting durations may then take place, e.g., over one or more characteristic durations. Longer periods of time are also conceivable, however, for example, an equalization of the lighting durations over a period of time that is longer than a characteristic duration, e.g., one minute. A variant of such an equalization is a change of the actuating signals for the individual lighting elements. In the example of four signals in FIG. 5, it would be conceivable to actuate different lighting elements with SIG 1 in different time intervals and analogously to proceed with SIG 2-4, e.g., in a rotation process. These time intervals could correspond, for example, to 1, 2, 3, 5, 10, 100 characteristic durations.

In the exemplary embodiment that is shown in FIG. 6, whether an illuminant or a lighting element 12 is on (activated) or off (deactivated) is characterized with "0" and "1," respectively. The Walsh subinterval is here again divided into two intervals. The assignment of ones and zeros changes per Walsh subinterval. Nevertheless, the desired brightness (25% or 75%) is always achieved. The advantage compared to the exemplary embodiment of FIG. 5 is that all the partial illuminants 12 are actually used. Heat and aging are thus distributed largely uniformly among all partial illuminants 12. It can be seen in the FIG. 6, e.g., that all partial illuminants 12 are precisely switched on four times and switched off four times in the time segment being shown. In addition to the assignments shown in FIG. 6, many other assignments, especially rotation patterns in the actuation may also be employed.

It is seen compared to FIG. 4 that the signals of FIG. 6 do not change their value during the PWM intervals. This has, on the one hand, the advantage that the signals have a lower frequency and, on the other hand, fewer scanning points are necessary for correct detection. One scanning value per PWM interval is sufficient in this case. In the example according to FIG. 5, a minimal scanning frequency of 1,000 Hz is obtained because the duration of the Walsh subinterval is 1 msec. In the exemplary embodiment according to FIG. 6, a scanning frequency of 2,000 Hz follows. Both are markedly lower than the above noted 8,000 Hz of the embodiment of FIG. 4.

In some exemplary embodiments, the scanning rate can therefore be reduced because of the smaller bandwidth of the analog signal processing (lower limit frequency). With the reduced scanning frequency, a marked reduction of the necessary computing power of the digital signal processing (processor, cloud capacity, etc.) 40 is also possible in some exemplary embodiments.

Detection of objects in a beam path of the lighting device 10 and control of the groups of lighting elements 20a-g based on the objects may also generally take place in the exemplary embodiments. As already explained above, the activation of the subset of a spatial modulation of the lighting elements of a group of lighting elements 20a-g may correspondingly correspond to the light intensities and a temporal modulation of the lighting elements of a group of lighting elements 20a-g may further take place. The spatial modulation and the temporal modulation may be simultaneous and/or offset in time in the exemplary embodiments.

The number of partial illuminants or lighting elements 12 per group of lighting elements 20a-g may be decisive for a possible gradation (granularity) of the brightness/light intensity (0, 25%, 50%, 75%, 100% in the above example). In order to achieve a finer gradation, more illuminants 12 may be used or even a combination of spatial and temporal modulation may be used. Very many LEDs 12 are used in some other exemplary embodiments. At least 20 LEDs are then necessary for a gradation in 5% increments in case of purely spatial modulation. The number of requests for an application (e.g., gradation in 5% increments) can easily be adapted by using, e.g., printable LEDs, which can be manufactured in large numbers at low costs.

The features disclosed in the above description, the claims and the drawings may be of importance both individually and in any desired combination for the attainment of exemplary embodiments in their different configurations and— unless something different appears from the description— may be combined with one another as desired.

Even though some aspects were described in connection with a device, it is apparent that these aspects also represent a description of the corresponding process, so that a block or a component of a device can also be defined as a corresponding process step or as a feature of a process step. Analogously hereto, aspects that were described in connection with a process step or as a process step also represent a description of a corresponding block or detail or feature of a corresponding device.

Depending on certain implementation requirements, exemplary embodiments of the controller 40 of the present invention may be implemented in hardware or in software. The implementation may be carried out with the use of a digital storage medium, for example, a floppy disk, a DVD, a Blu-Ray disk, a CD, a ROM, a PROM, an EPROM, an EEPROM or a FLASH memory, a hard drive or another magnetic or optical memory, on which electronically readable control signals are stored, which can or do interact with a programmable hardware component or a cloud such that the corresponding process is carried out.

A programmable hardware component of the controller 40 may be formed by a processor, a computer processor (CPU=Central Processing Unit), a graphics processor (GPU=Graphics Processing Unit), a computer, a computer system, an application-specific integrated circuit (ASIC=Application-Specific Integrated Circuit), an integrated circuit (IC=Integrated Circuit), a system-on-chip system (SOC=System on Chip), a programmable logic element or a field-programmable gate array with a microprocessor (FPGA=Field-Programmable Gate Array).

The digital storage medium (memory) of the controller 40 may therefore be machine- or computer-readable. Some exemplary embodiments consequently comprise a data storage medium, which has electronically readable control signals, which are capable of interacting with a programmable computer system or with a programmable hardware component such that one of the processes being described here is executed. An exemplary embodiment is thus a data storage medium (or a digital storage medium or a computer-readable medium), on which the program for executing a process being described here is stored.

Exemplary embodiments of the process 50 of the present invention may generally be implemented as a program, firmware, computer program or computer program product with a program code or as data, wherein the program code or the data acts/act such as to execute one of the processes when the program is being run on a processor or on a programmable hardware component. The program code or the data may also be stored, for example, on a machine-readable carrier or data storage medium. The program code or the data may be present, among other things, as source code, machine code or byte code as well as another intermediate code.

Another exemplary embodiment is provides a computer/controller 40 spaced apart from the groups of lighting elements 20a-g, associated with a transceiver/communication interface, wherein the process 50 may be implemented with a data stream, a signal sequence or a sequence of signals, which data stream or sequence represents/represent the program for executing one of the processes steps of the process 50. The data stream, the signal sequence or the sequence of signals may be configured, for example, such as to be transferred via a data communication link, for example, via the Internet or another network. Exemplary embodiments are thus also signal sequences representing data, which are suitable for transmission via a network or a data communication link (communication interface), wherein the data represent the program executing one of the processes steps of the process 50.

A program according to an exemplary embodiment may implement one of the processes steps of the process 50 while the program is being executed, for example, by reading storage locations or writing a datum or a plurality of data in these locations, as a result of which switching operations or other operations are elicited in transistor structures, in amplifier structures or in other electrical, optical, magnetic components or components operating according to another principle of operation. Correspondingly, data, values, sensor values or other information can be detected, determined or measured by a program by reading a storage location. A program can therefore detect, determine or measure variables, values, measured variables and other information by reading from one or more storage locations and bring about, prompt or carry out an action by writing in one or more storage locations as well as actuate other devices, machines and components.

The above-described exemplary embodiments only represent an illustration of the principles of the present invention. It is obvious that modifications and variations of the arrangements and details being described here will be obvious to other persons skilled in the art. The present invention is therefore intended to be limited only by the scope of protection of the following patent claims rather than by the specific details, which were presented here on the basis of the description and the explanation of the exemplary embodiments. While specific embodiments of the invention have been shown and described in detail to illustrate the application of the principles of the invention, it will be understood that the invention may be embodied otherwise without departing from such principles.

What is claimed is:

1. A process for controlling a plurality of lighting elements in a lighting device, wherein the plurality of lighting elements are divided into a plurality of groups of lighting elements with each group of lighting elements comprising at least two lighting elements, the process comprising:
    assigning a characteristic to each of the plurality of groups of lighting elements, wherein the characteristic assigned to said each group of lighting elements is different from the characteristic assigned to each other group of the plurality of groups of lighting elements and each characteristic comprises a characteristic duration and comprises a predetermined sequence of different light intensities of a respective each group as a whole in temporal subintervals, wherein the predetermined sequence is repeated at an end of the characteristic duration; and
    activating subsets of lighting elements in the plurality of groups of lighting elements in the temporal subintervals based on the predetermined sequence of different light intensities for a plurality of the characteristic durations, said each group performing a respective same said predetermined sequence in each of the plurality of the characteristic durations, the activating subsets of lighting elements in the plurality of groups of lighting elements in the temporal subintervals based on the predetermined sequence of different light intensities comprises a spatial modulation of the lighting elements of one of the plurality of groups of lighting elements corresponding to the predetermined sequence of different light intensities.

2. The process in accordance with claim 1, wherein the activating of the subsets of lighting elements of a group of lighting elements comprises, for each of the subsets of lighting elements, an activation of at least one lighting element of the group of lighting elements and a simultaneous deactivation of at least one other lighting element of the group of lighting elements in a subinterval, upon a light intensity being a minimal light intensity in the temporal subinterval.

3. The process in accordance with claim 1, wherein:
    the predetermined sequence of different light intensities comprise at least one higher light intensity and at least one lower light intensity;
    at least one lighting element of said one, or another one, of the plurality of groups of lighting elements is activated and another lighting element of said one, or said another one, of the plurality of groups of lighting elements is deactivated in a subinterval with the at least one lower light intensity.

4. The process in accordance with claim 1, wherein the plurality of groups of lighting elements are arranged spatially or geometrically separated.

5. The process in accordance with claim 4, wherein the plurality of groups of lighting elements are logically separated based on the characteristic.

6. The process in accordance with claim 1, wherein the characteristic corresponds to Walsh functions.

7. The process in accordance with claim 1, further comprising varying the activated subset of lighting elements of the subset of lighting elements of said one, or another one, of the plurality of groups of lighting elements.

8. The process in accordance with claim 7, wherein the varying of the activated subset of lighting elements comprises equalizing lighting durations of the plurality of lighting elements.

9. The process in accordance with claim 8, wherein the equalizing of lighting durations is carried out within a subinterval.

10. The process in accordance with claim 8, wherein the equalizing of lighting durations is carried out over one or more characteristic durations.

11. The process in accordance with claim 8, wherein the equalizing of lighting durations is carried out over a period of time that is longer than the characteristic duration.

12. The process in accordance with claim 1, further comprising detecting objects in a beam path of the lighting device and controlling the plurality of groups of lighting elements based on one or more objects detected.

13. The process in accordance with claim 1, wherein:
    the activating subsets of lighting elements in the plurality of groups of lighting elements in the temporal subintervals based on the predetermined sequence of different light intensities comprises the spatial modulation of the lighting elements of said one, or another one, of the plurality of groups of lighting elements and a temporal modulation of the lighting elements of the plurality of groups of lighting elements.

14. The process in accordance with claim 13, wherein the spatial modulation and the temporal modulation are carried out simultaneously or carried out at different times.

15. The process in accordance with claim 1, wherein:
    program code executes at least a portion of the process; and
    the program code is executed on a computer, on a processor or on a programmable hardware component.

16. A lighting device comprising:
    a plurality of lighting elements divided into a plurality of groups of lighting elements wherein each of the plurality of groups of lighting elements comprises at least two lighting elements; and
    a controller configured to:
    assign a characteristic to each of the plurality of groups of lighting elements, wherein the characteristic assigned to said each of the plurality of groups of lighting elements must be different from the characteristic assigned to each other group of the plurality of groups of lighting elements and each characteristic comprises a characteristic duration and comprises a predetermined sequence of different light intensities of a respective each group of the plurality of groups as a whole in temporal subintervals, wherein the predetermined sequence is repeated at an end of the characteristic duration; and
    activate subsets of lighting elements in the plurality of groups of lighting elements in the temporal subintervals based on the predetermined sequence of different light intensities for a plurality of the characteristic durations, said each group performing a respective same said predetermined sequence in each of the plurality of the characteristic durations.

17. The lighting device in accordance with claim 16, wherein the plurality of groups of lighting elements are arranged spatially separated or geometrically separated.

18. The lighting device in accordance with claim 16, wherein the activating of the subsets of lighting elements of a group of lighting elements comprises, for each of the subsets of lighting elements, an activation of at least one lighting element of one of the group of lighting elements and a simultaneous deactivation of at least one other lighting element of the one group of lighting elements in a subinterval, upon a light intensity being a minimal light intensity in the temporal subinterval.

19. The lighting device in accordance with claim 16, wherein:
 the controller is configured to activate the subsets of lighting elements in the plurality of groups of lighting elements in the temporal subintervals based on the predetermined sequence of different light intensities by spatial modulation of the lighting elements of one of the plurality of groups of lighting elements corresponding to the predetermined sequence of different light intensities of respective characteristics.

20. A process for controlling a lighting device, the process comprising the steps of:
 providing a plurality of lighting elements in the lighting device;
 dividing said plurality of lighting elements into a plurality of groups of lighting elements, each group of lighting elements including at least two of said plurality of lighting elements,
 providing a plurality of sequences of different light intensities, each sequence of the plurality of sequences being different from each other sequence, said each sequence of the plurality of sequences having a period;
 activating each group of lighting elements to emit light for a plurality of said period, said each group emits light in each of said plurality of period according to just one of the plurality of sequences, said each group emits light according to a respective one sequence of different light intensities for each of the plurality of durations, said each group emitting light according to a different one of the plurality of sequences of different light intensities than each other group of the plurality of groups.

21. The process in accordance with claim 20, wherein:
 said each group of lighting elements emits the different light intensities by selectively actuating varying amounts of said plurality of lighting elements and selectively deactivating other said plurality of lighting elements in the respective said each group of the plurality of groups of lighting elements.

22. The process in accordance with claim 21, wherein:
 said selectively actuating spatially modulates which lighting elements are activated.

* * * * *